US009301703B2

(12) United States Patent
Sato

(10) Patent No.: US 9,301,703 B2
(45) Date of Patent: Apr. 5, 2016

(54) BIOLOGICAL INFORMATION PROCESSING DEVICE, BIOLOGICAL INFORMATION PROCESSING SYSTEM, BIOLOGICAL INFORMATION COMPRESSION METHOD, AND BIOLOGICAL INFORMATION COMPRESSION PROCESSING PROGRAM

(71) Applicant: KYUSHU INSTITUTE OF TECHNOLOGY, Kitakyushu-shi (JP)

(72) Inventor: Yasushi Sato, Kitakyushu (JP)

(73) Assignee: KYUSHU INSTITUTE OF TECHNOLOGY, Kitakyushu-Shi, Fukuoka (JP)

( * ) Notice: Subject to any disclaimer, the term of this patent is extended or adjusted under 35 U.S.C. 154(b) by 0 days.

(21) Appl. No.: 14/372,982

(22) PCT Filed: Dec. 19, 2012

(86) PCT No.: PCT/JP2012/082934
§ 371 (c)(1),
(2) Date: Jul. 17, 2014

(87) PCT Pub. No.: WO2013/118398
PCT Pub. Date: Aug. 15, 2013

(65) Prior Publication Data
US 2015/0005655 A1    Jan. 1, 2015

(30) Foreign Application Priority Data

Feb. 8, 2012  (JP) ................................ 2012-025447

(51) Int. Cl.
*A61B 5/04*    (2006.01)
*A61B 5/0456*  (2006.01)
*A61B 5/00*    (2006.01)

(52) U.S. Cl.
CPC ............. *A61B 5/0456* (2013.01); *A61B 5/0006* (2013.01); *A61B 5/7232* (2013.01); *A61B 5/7239* (2013.01); *A61B 5/7253* (2013.01); *A61B 5/7278* (2013.01)

(58) Field of Classification Search
CPC .. A61B 5/0456; A61B 5/0452; A61B 5/0402; A61B 5/7253; A61B 5/72535; A61B 5/72
See application file for complete search history.

(56) References Cited

U.S. PATENT DOCUMENTS 4,633,884 A * 1/1987 Imai et al. ..................... 600/509
6,152,883 A   11/2000 Blanchett et al.
(Continued)

FOREIGN PATENT DOCUMENTS

JP    5-056943 A    3/1993
JP    8-299293 A    11/1996
(Continued)

OTHER PUBLICATIONS

International Search Report (PCT/ISA/210) mailed on Apr. 2, 2013, by the Japanese Patent Office as the International Searching Authority for International Application No. PCT/JP2012/082934.
(Continued)

*Primary Examiner* — Robert N Wieland
(74) *Attorney, Agent, or Firm* — Buchanan Ingersoll & Rooney PC

(57) ABSTRACT

This biological information processing device is provided with: a peak detection unit for detecting the peaks of a biological signal generated in a cardiac cycle; a waveform clipping unit for clipping out a first peak-to-peak biological signal between two peaks, which are adjacent on the time axis of the biological signal, on the basis of detection results of the peak detection unit; and a resampling unit for transforming the first peak-to-peak biological signal to a second peak-to-peak biological signal for a prescribed number of samples. The biological information processing device is further provided with: an orthogonal transformation unit for generating orthogonal transformation coefficients by performing an orthogonal transformation on the second peak-to-peak biological signal; a differential processing unit for generating a differential signal for the orthogonal transformation coefficients on the time axis; and an encoding unit for encoding the differential signal.

12 Claims, 8 Drawing Sheets

(56) References Cited

U.S. PATENT DOCUMENTS

| | | | |
|---|---|---|---|
| 2002/0143263 A1* | 10/2002 | Shusterman | 600/509 |
| 2003/0083581 A1 | 5/2003 | Taha et al. | |
| 2003/0093271 A1 | 5/2003 | Tsushima et al. | |
| 2008/0109041 A1* | 5/2008 | de Voir | 607/7 |

FOREIGN PATENT DOCUMENTS

| | | |
|---|---|---|
| JP | 11-267107 A | 10/1999 |
| JP | 2002-159451 A | 6/2002 |
| JP | 2009-022639 A | 2/2009 |

OTHER PUBLICATIONS

Asl, B. M., et al. "Support Vector Machine-based Arrhythmia Classification Using Reduced Features of Heart Rate Variability Signal.", Artificial Intelligence in Medicine, Sep. 1, 2008, pp. 51-64, vol. 44, No. 1.

Batista, Leonardo Vidal, et al. "Compression of ECG Signals by Optimized Quantization of Discrete Cosine Transform Coefficients", Medical Engineering & Physics, Jan. 1, 2001, pp. 127-134, vol. 23.

Jalaleddine et al., "EGG Data Compression Techniques—A Unified Approach" IEEE Transactions on Biomedical Engineering, Apr. 1, 1990, pp. 329-343, vol. 37, No. 4.

Shi, Zhuoer et al., "Generalized Symmetric Interpolating Wavelets", Computer Physics Communications, pp. 194-218, vol. 119, No. 2-3.

Kumar, V., et al. "Direct Data Compression of ECG Signal for Telemedicine", International Journal of Systems Science, pp. 45-63, vol. 37, No. 1.

Bendifallah, A., et al., "Improved ECG Compression Method Using Discrete Cosine Transform", Electronics Letters, Jan. 20, 2011, pp. 87-89, vol. 47, No. 2.

Extended European Search Report issued on Aug. 5, 2015, by the European Patent Office in European Patent Application No. 12868191.3-1657.

* cited by examiner

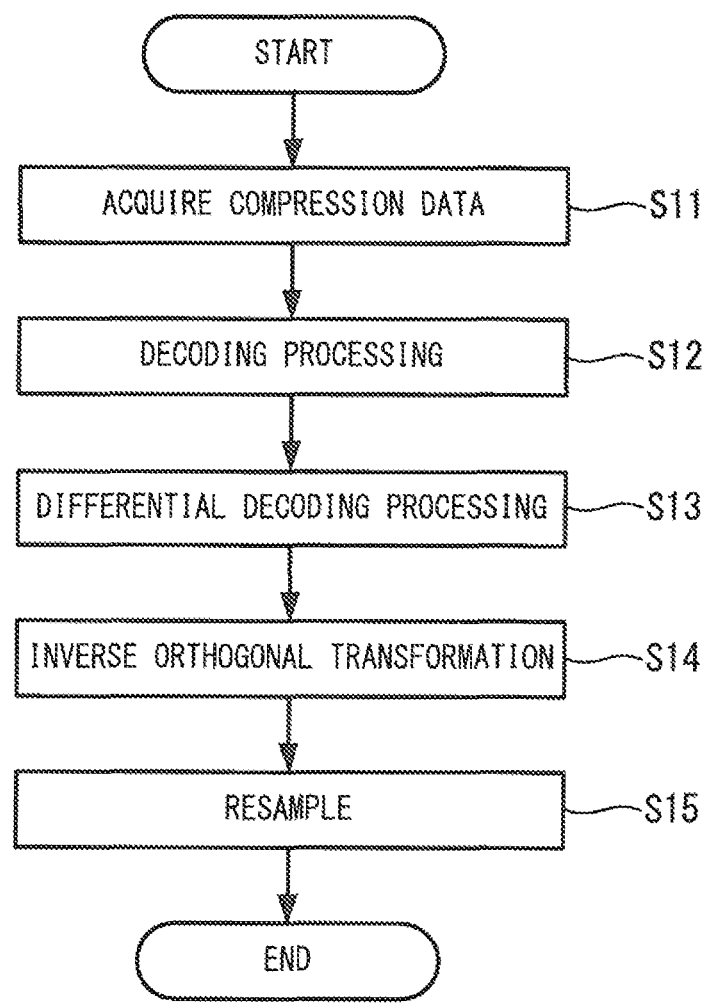

BIOLOGICAL INFORMATION PROCESSING DEVICE, BIOLOGICAL INFORMATION PROCESSING SYSTEM, BIOLOGICAL INFORMATION COMPRESSION METHOD, AND BIOLOGICAL INFORMATION COMPRESSION PROCESSING PROGRAM

TECHNICAL FIELD

The present invention relates to biological information processing devices, biological information processing systems, biological information compression methods, and biological information compression processing programs provided with a function to compress biological information, such as electrocardiographic information and pulse wave information.

BACKGROUND ART

When the waveform data of a biological signal, such as an electrocardiographic signal, is compressed, the waveform of the biological signal may significantly deteriorate and affect medical decision. Therefore, usually, the compression processing is not performed on the biological signal. However, recently, there are also increased opportunities for remote medical care and storage of biological information, and various kinds of techniques also have been proposed, which compress a biological signal using an audio compression technique and output the compressed biological information to an external terminal or memory (e.g., see Patent Literatures 1, 2).

Patent Literature 1 proposes a medical terminal device that compresses the electrocardiographic data converted to digital data and outputs the compressed electrocardiographic data to a device on the doctor side via a telephone line. Patent Literature 2 proposes a Holter monitor device that compresses digital-converted electrocardiographic data using a wavelet code transformation method and stores the compressed electrocardiographic data into an external nonvolatile memory.

CITATION LIST

Patent Literature

Patent Literature 1: Japanese Patent Laid-Open No. 2002-159451
Patent Literature 2: Japanese Patent Laid-Open No. 1996-299293

SUMMARY OF INVENTION

Technical Problem

Because the waveform of a biological signal, such as an electrocardiographic signal, is usually an impulse-shaped waveform, the information on up to a relatively high frequency band is needed in order to precisely decode a compressed biological signal. Therefore, with the conventional audio compression technique, it is difficult to compress biological information at a sufficiently high compression rate (e.g., compression rate higher than $1/10$). Moreover, in transmitting biological information via a communication network, the biological information needs to be compressed at a higher compression rate.

The present invention has been made in view of the above circumstances, and an object of the present invention is to provide a biological information processing device, a biological information processing system, a biological information compression method, and a biological information compression processing program capable of compressing biological information at a higher compression rate.

Solution to Problem

In order to solve the above-described problems, a first biological information processing device according to the present invention includes: a peak detection unit configured to detect peaks of a biological signal generated in a cardiac cycle; a waveform clipping unit configured to clip out a first peak-to-peak biological signal between two peaks, which are adjacent on a time axis of the biological signal, on the basis of detection results of the peak detection unit; a resampling unit configured to transform the first peak-to-peak biological signal to a second peak-to-peak biological signal of a prescribed number of samples; an orthogonal transformation unit configured to generate orthogonal transformation coefficients by performing an orthogonal transformation on the second peak-to-peak biological signal; a differential processing unit configured to generate a differential signal of the orthogonal transformation coefficients on the time axis; and an encoding unit configured to encode the differential signal.

Note that, the "biological signal (biological information)" as used herein refers to a biological signal (biological information) whose amplitude varies substantially-periodically in synchronization with a cardiac cycle, such as an electrocardiographic signal or a pulsebeat signal.

A second biological information processing device according to the present invention includes: a control unit configured to control operations of processes of: detecting peaks of a biological signal generated in a cardiac cycle; clipping out a first peak-to-peak biological signal between two peaks, which are adjacent on a time axis of the biological signal, on the basis of detection results of the peaks; transforming the first peak-to-peak biological signal to a second peak-to-peak biological signal of a prescribed number of samples; performing an orthogonal transformation on the second peak-to-peak biological signal to generate orthogonal transformation coefficients; generating a differential signal of the orthogonal transformation coefficients on the time axis; and encoding the differential signal.

A biological information processing system according to the present invention includes the first biological information processing device according to the present invention and a biological information decoding device that decodes a biological signal from the signal encoded by the encoding unit.

Furthermore, with a biological information compression method and a compression processing program according to the present invention, the peaks of a biological signal generated in a cardiac cycle are detected first. Next, on the basis of detection results of the peak, a first peak-to-peak biological signal between two peaks, which are adjacent on a time axis of the biological signal, is clipped out. Next, the first peak-to-peak biological signal is transformed to a second peak-to-peak biological signal of a prescribed number of samples. Next, orthogonal transformation coefficients are generated by performing an orthogonal transformation on the second peak-to-peak biological signal. Next, a differential signal of the orthogonal transformation coefficients on the time axis is generated. Then, the difference signal is encoded.

Advantageous Effects of Invention

As described above, in the biological information compression technique according to the present invention, the first peak-to-peak biological signal clipped out from a biological signal is transformed (normalized) to the second peak-to-peak biological signal of a prescribed number of samples. Furthermore, in the present invention, the encoding processing is performed on a differential signal between the orthogonal transformation coefficients of the normalized second peak-to-peak biological signal so as to compress the biological signal. Therefore, according to the present invention, biological information can be compressed at a higher compression rate.

BRIEF DESCRIPTION OF DRAWINGS

FIG. 10 is a flow chart illustrating a procedure of electrocardiographic information decoding processing in the biological information decoding device according to an embodiment of the present invention.

DESCRIPTION OF EMBODIMENTS

Hereinafter, an example of a biological information processing device, a biological information processing system, and a biological information compression method according to an embodiment of the present invention is described with reference to the accompanying drawings. Note that, in the description below, as a biological signal, an electrocardiographic signal is taken as the example and described, but the present invention is not limited thereto. The compression technique according to the present invention can be applied to any biological signal whose amplitude varies substantially-periodically in synchronization with a cardiac cycle, such as a pulsebeat signal, and the same effect can be obtained.

<1. Operation Principle of Compression and Decoding of Biological Information>

[Compression Principle of Electrocardiographic Signal]

Figure 1:
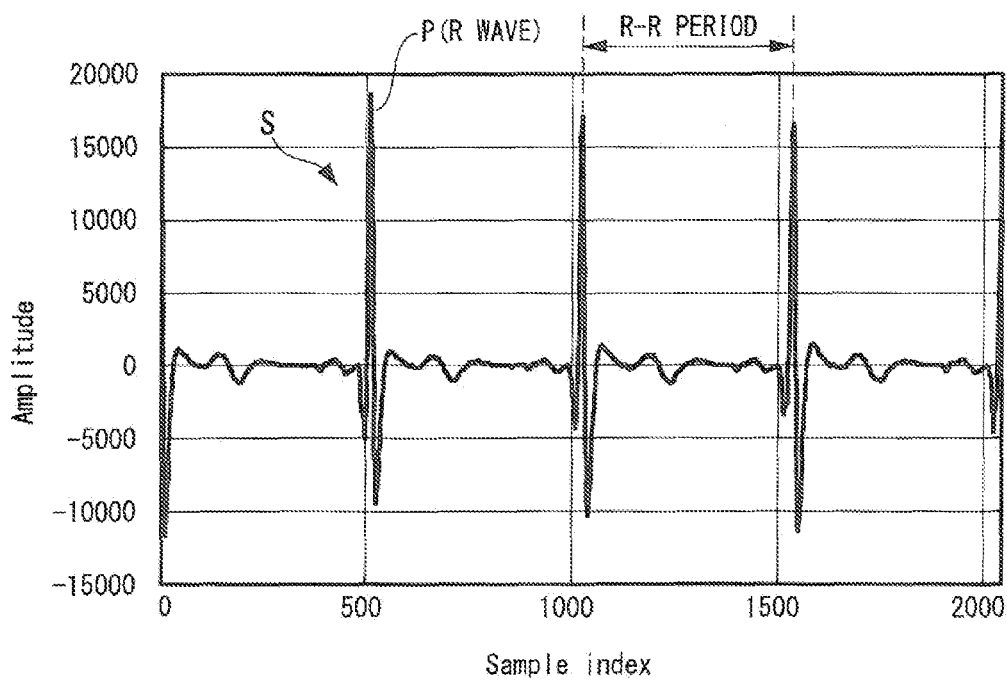
FIG. 1 is a waveform chart of an electrocardiographic signal.

First, the principle of an electrocardiographic information compression method in the present invention is described. FIG. 1 illustrates an example of the waveform of an electrocardiographic signal. Note that, the horizontal axis of the characteristics illustrated in FIG. 1 represents a sample index on the time axis (i.e., the horizontal axis is the time axis), while the vertical axis represents the amplitude of an electrocardiographic signal S.

Usually, in the waveform of the electrocardiographic signal S, as illustrated in FIG. 1, peaks P (peak generated in a cardiac cycle) of an R wave are generated substantially at an equal interval. On the time axis (on the horizontal axis of FIG. 1), the signal waveform in the period (hereinafter, referred to as the R-R period) between two peaks P of the R wave adjacent to each other, is repeatedly generated in substantially the same waveform. However, the generation cycle (R-R period) of the peak P of the R wave is not always constant but varies slightly, i.e., a fluctuation is generated in the generating position of the peak P of the R wave. In the present invention, this fluctuation of the electrocardiographic waveform is removed and compression processing is performed on the electrocardiographic signal S whose fluctuation is removed.

Figure 2:
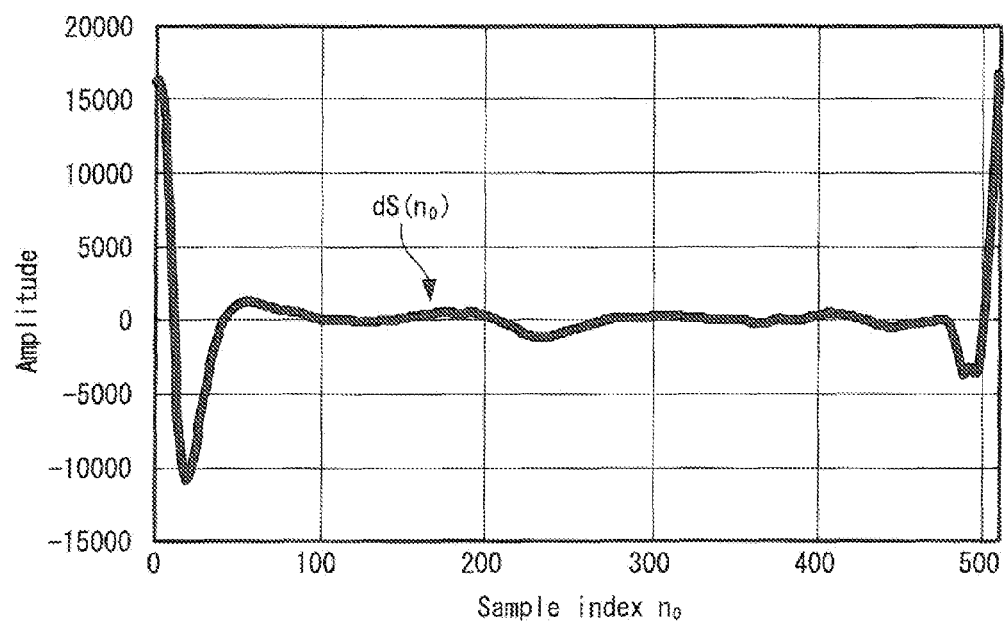
FIG. 2 is a waveform chart of the electrocardiographic signal clipped out in an R-R period.

Specifically, first, from the detected electrocardiographic signal S, an electrocardiographic signal is clipped out (extracted) for each R-R period. FIG. 2 illustrates an example of the waveform of the clipped electrocardiographic signal dS(n0) (n0 is a sample index (0 to N0-1) on the time axis) in the R-R period. Note that, the horizontal axis of the characteristic illustrated in FIG. 2 represents the sample index n0 on the time axis, while the vertical axis represents the amplitude of the electrocardiographic signal.

As described above, the R-R period also varies slightly because there is a fluctuation in the generating position of the peak P of the R wave. Therefore, the number of samples NO (sampling number) of the electrocardiographic signal dS(n0) (hereinafter, referred to as an inter-peak electrocardiographic signal dS(n0)) clipped out in the R-R period also varies depending on a time zone to clip out.

Then, in the present invention, the inter-peak electrocardiographic signal dS(n0) is resampled (normalized) with a prescribed number of samples N, so that the number of samples of all the inter-peak electrocardiographic signals after resampling processing is set constant. Note that, as the resampling method, a method, such as a Lagrange's method or a spline method, can be used. The number of samples N in resampling may be larger or smaller than the number of samples NO of the inter-peak electrocardiographic signal dS(n0).

Figure 3A:
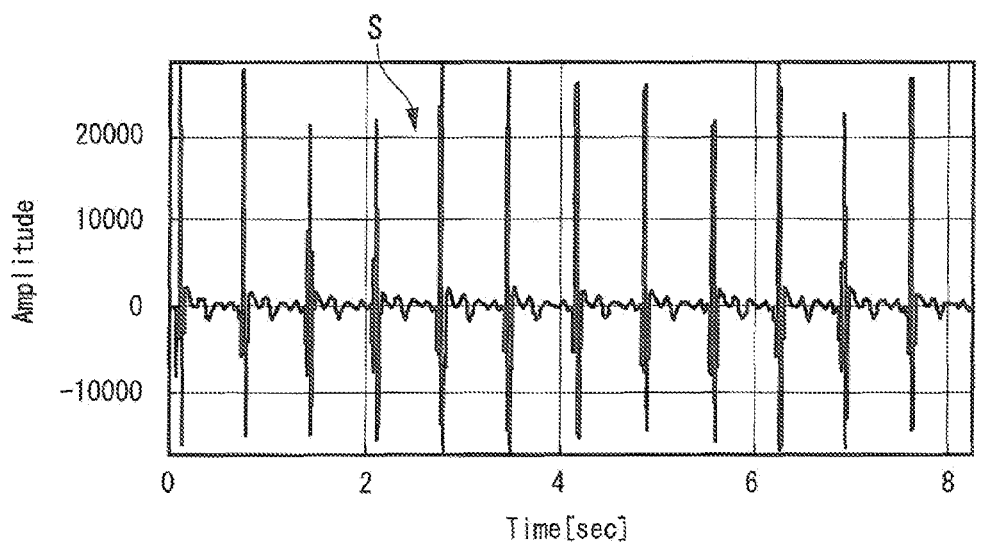
FIGS. 3A and 3B are waveform charts of an electrocardiographic signal before and after resampling processing, respectively.
Figure 3B:
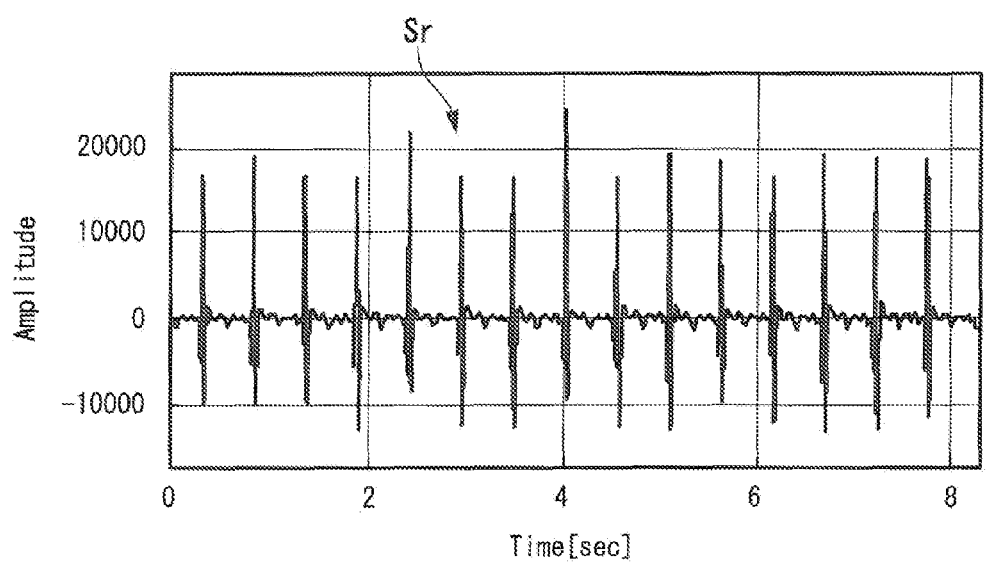

FIGS. 3A and 3B illustrate the waveforms of the electrocardiographic signals S before resampling processing and the waveforms of the electrocardiographic signals Sr after resampling processing, respectively. Note that, the horizontal axis of the characteristics illustrated in FIGS. 3A and 3B represents the time, while the vertical axis represents the amplitude of the electrocardiographic signal. FIGS. 3A and 3B illustrate an example in the case where the number of samples N in resampling is set smaller than the minimum value of the number of samples NO of the inter-peak electrocardiographic signal dS(n0).

In the electrocardiographic signal Sr after resampling processing, in which the resampled (normalized) inter-peak electrocardiographic signals (x(n) to be described later) are arranged in chronological order, the generation cycle (R-R period) of the peak P of the R wave is constant. That is, the inter-peak electrocardiographic signal dS(n0) of actual data is resampled, so that in the electrocardiographic signal Sr after resampling processing, the above-described fluctuation in the generating position of the peak P of the R wave (a fluctuation of the R-R period) is removed. Moreover, due to this resampling processing, the waveforms of the inter-peak electrocardiographic signal x(n) normalized in each R-R period have mutually similar shapes regardless of the time zone of the R-R period.

Next, the normalized inter-peak electrocardiographic signal x(n) (n is the sample index (0 to N-1) on the time axis) is divided into a prescribed number (in an embodiment to be described later, the same number as the number of samples N of the normalized inter-peak electrocardiographic signal x(n)) of frequency bands to be subjected to orthogonal transformation. In this case, as the orthogonal transformation method, a method, such as DCT (Discrete Cosine Transform), MDCT (Modified DCT), LOT (Lapped Orthogonal Transform), or WHT (Walsh-Hadamard Transform), can be used.

By the above-described orthogonal transformation, the inter-peak electrocardiographic signal x(n) in the time domain is transformed to a signal in the frequency domain, i.e., to an orthogonal transformation coefficient X(k) (k is the index of a divided frequency band). Once the normalized inter-peak electrocardiographic signal x(n) is subjected to orthogonal transformation in this manner, the high frequency components in the inter-peak electrocardiographic signal x(n) are transformed to an integer (DC component) and is therefore transformed to the data easy to be compressed (data that can be compressed at a high compression rate).

Moreover, as described above, the waveforms of the normalized inter-peak electrocardiographic signal x(n) have mutually similar shapes regardless of the time zone of the R-R period, and therefore the difference between an orthogonal transformation coefficient X(k) calculated in a prescribed R-R period and an orthogonal transformation coefficient X(k) calculated in the R-R period immediately before or immediately after the prescribed R-R period, decreases. That is, the orthogonal transformation coefficient X(k) calculated for each R-R period varies continuously and gently with respect to time.

Figure 4:
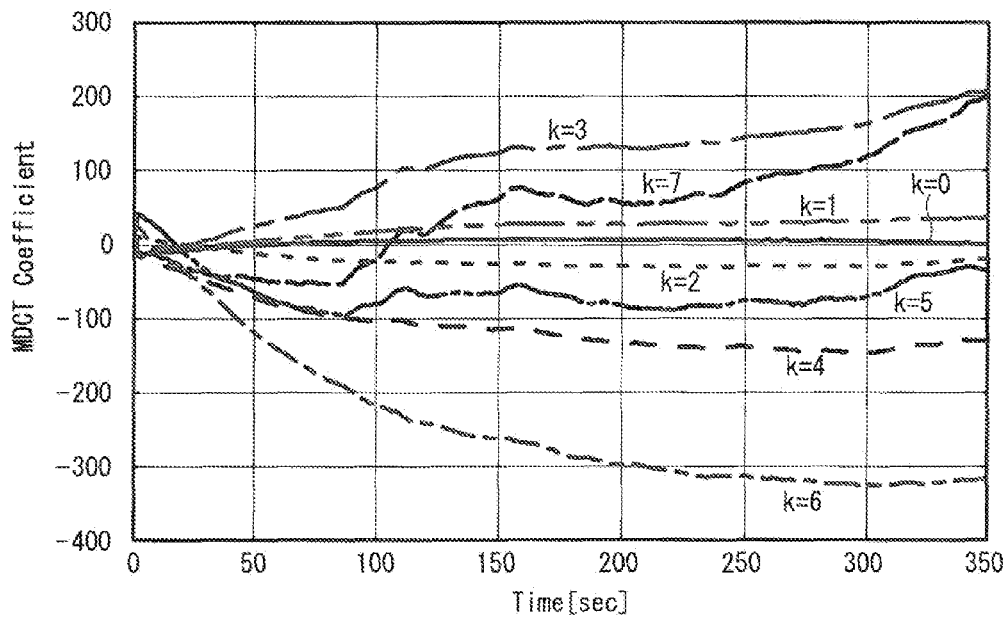
FIG. 4 is a graph illustrating the time change characteristics of orthogonal transformation coefficients.

FIG. 4 illustrates an example of the time change characteristics of the orthogonal transformation coefficient X(k). FIG. 4 illustrates the time change characteristic of the orthogonal transformation coefficient X(k) that is obtained when the normalized inter-peak electrocardiographic signal x(n) is subjected to orthogonal transformation by MDCT. Note that, the horizontal axis of the characteristics illustrated in FIG. 4 represents time, while the vertical axis represents the value of the MDCT coefficient (X(k)). The characteristics illustrated in FIG. 4 are the characteristics when each MDCT coefficient calculated for each R-R period is plotted sequentially in chronological order. FIG. 4 illustrates the time change characteristic of each MDCT coefficient of k=0 to 7. As apparent also from FIG. 4, it can be seen that by performing an orthogonal transformation on the normalized inter-peak electrocardiographic signal x(n) by MDCT, the value of the orthogonal transformation coefficient X(k) (MDCT coefficient) varies continuously and gently with respect to time.

Next, in the present invention, a differential signal dX(k) of the orthogonal transformation coefficient X(k) is calculated on the time axis. As described above, the value of the orthogonal transformation coefficient X(k) varies continuously and gently with respect to time. Therefore, the time series data of the differential signal dX(k) obtained by this differential processing is not the data in which the value of the differential signal dX(k) varies for each sample, but the data in which the differential signal dX(k) of the same value is continuously arranged for a prescribed period. That is, the format of the time series data of the differential signal dX(k) results in a format that can be easily compressed at a higher compression rate by conventionally known encoding processing.

Note that, the method for calculating the differential signal dX(k) is arbitrary, and for example, simply, a difference value between an orthogonal transformation coefficient X(k) at a prescribed time t and an orthogonal transformation coefficient X(k) at a time t−1 immediately before the prescribed time t (at the time one sample earlier than the prescribed time t on the time axis) or at a time t+1 immediately after the prescribed time t (at the time one sample later than the prescribed time t on the time axis) may be set to the differential signal dX(k). Moreover, a signal that is obtained by encoding this difference value using a method, such as DPCM (Differential Pulse Code Modulation) or ADPCM (Adaptive DPCM), may be set to the differential signal dX(k). In the case where the method of DPCM or ADPCM is used, the amount of data can be further reduced because both the difference calculation processing and the quantization (encoding) processing will be actually performed on the orthogonal transformation coefficient X(k).

Then, the conventionally-known reversible encoding processing, such as an entropy-encoding processing (Huffman code, arithmetic code, LZH code, LZSS code, or the like), is performed on the time series data of the differential signal dX(k) of the orthogonal transformation coefficient X(k) that is calculated as described above. In the present invention, electrocardiographic information is compressed based on the above-described principle.

As described above, the electrocardiographic information compression method according to the present invention makes maximum use of the characteristics of the waveform shape of the electrocardiographic signal S in which the substantially the same shaped waveform is repeated substantially-periodically, and can achieve a very high compression rate as compared with the conventional compression method (the method in which the inter-peak electrocardiographic signal dS(n0) is not normalized with a prescribed number of samples N). For example, the compression rate of the conventional compression method is approximately ⅒ at the most, but the compression rate on the order of ¹⁄₁₀₀ can be achieved with the compression method according to the present invention.

[Principle on Electrocardiographic Information Expansion and Decoding]

Next, the principle on the expansion and decoding method of the compressed electrocardiographic signal Sc is described. In the present invention, basically, processing opposite to the above-described compression processing of the electrocardiographic signal S is applied to perform the expansion and decoding of the compressed electrocardiographic signal Sc.

First, decoding processing is performed on the electrocardiographic signal Sc, which is compressed based on the above-described principle, so as to decode the time series data of the differential signal dX(k) of the orthogonal transformation coefficient X(k). Note that, in this case, the time series data of the differential signal dX(k) is decoded using decoding processing corresponding to the encoding processing that is used in compressing the electrocardiographic signal S.

Next, the orthogonal transformation coefficient X(k) is calculated from the time series data of the decoded differential signal dX(k) (differential decoding processing). Note that, in this case, the orthogonal transformation coefficient X(k) is decoded using a decoding method corresponding to the method for calculating the differential signal dX(k) that is used in compressing the electrocardiographic signal S.

Next, the orthogonal transformation coefficient X(k) is subjected to inverse orthogonal transformation. Thus, the orthogonal transformation coefficient X(k) in the frequency domain is transformed to the normalized inter-peak electrocardiographic signal x(n) in the time domain. Note that, in this case, the normalized inter-peak electrocardiographic signal x(n) is calculated using an inverse orthogonal transformation method (e.g., IDCT (Inverse DCT), IMDCT (Inverse MDCT), or the like) corresponding to the orthogonal transformation method that is used in compressing the electrocardiographic signal S.

Next, the normalized inter-peak electrocardiographic signal x(n) is resampled with the number of samples NO of actual data (dS(n0)) of the corresponding inter-peak electrocardiographic signal to calculate the actual data (dS(n0)) of the inter-peak electrocardiographic signal. Note that, in this case, as the resampling method, the same method as the resampling method (e.g., Lagrange's method, spline method, or the like) that is used in compressing the electrocardiographic signal S is preferably used. Then, the inter-peak electrocardiographic signals dS(n0) obtained as described above are combined sequentially in chronological order so as to decode the actual data of the electrocardiographic signal S.

<2. Example of Configuration of Biological Information Processing System (Biological Information Processing Device)>

Next, an example of the configuration of the biological information processing system, the biological information processing device, and the biological information decoding device for achieving the above-described operation principle of the electrocardiographic information compression and decoding is described.

[Biological Information Processing System]

Figure 5:
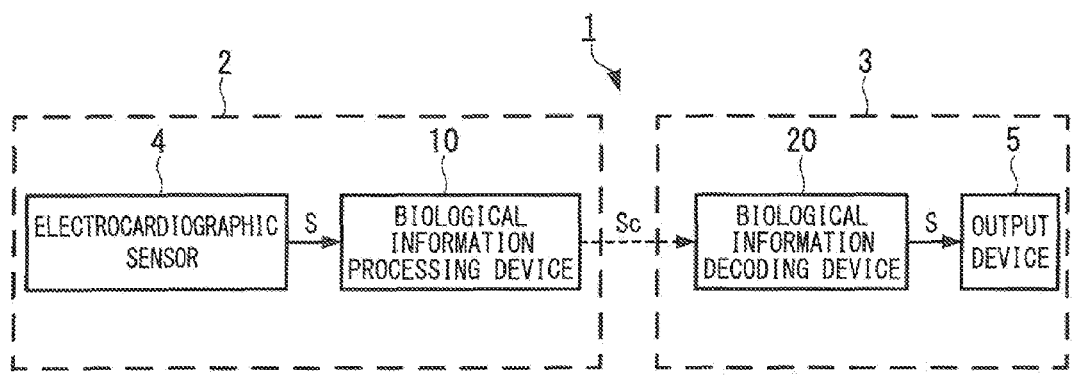
FIG. 5 is a general block configuration diagram of a biological information processing system according to an embodiment of the present invention.

FIG. 5 illustrates the general block configuration of the biological information processing system according to an embodiment of the present invention. A biological information processing system 1 includes an electrocardiographic information transmission-side device 2 and an electrocardiographic information receiving-side device 3. In the example illustrated in FIG. 5, for example, the transmission-side device 2 is provided on a patient side, while the receiving-side device 3 is provided on a facility side, such as a hospital, where health care of the patient is performed. Note that, in the embodiment, an example is described, in which electrocardiographic information is transmitted from the transmission-side device 2 to the receiving-side device 3 via wireless communication or wired communication.

The transmission-side device 2 has an electrocardiographic sensor 4 and a biological information processing device 10 electrically connected to the electrocardiographic sensor 4.

The electrocardiographic sensor 4 is attached to a patient and detects the patient's electrocardiographic signal. Then, the electrocardiographic sensor 4 outputs the detected electrocardiographic signal S (electrocardiographic information) to the biological information processing device 10.

The biological information processing device 10 can be constituted by a device, such as a personal computer, a portable communication terminal device, or a dedicated information processing device. The biological information processing device 10 acquires the patient's electrocardiographic signal S (electrocardiographic data) from the electrocardiographic sensor 4. Next, the biological information processing device 10 compresses the acquired electrocardiographic signal S using the above-described compression method. Then, the biological information processing device 10 transmits a compressed electrocardiographic signal Sc to the receiving-side device 3 via communication. Note that the internal configuration and more detailed operation (function) of the biological information processing device 10 are described later.

The receiving-side device 3 has an output device 5 and a biological information decoding device 20 electrically connected to the output device 5.

The output device 5 can be constituted by a device, such as a display device for displaying an image of the decoded electrocardiographic signal S or a printing device for printing out the electrocardiographic signal S.

The biological information decoding device 20 can be constituted by a device, such as a personal computer, a portable communication terminal device, or a dedicated information processing device. The biological information decoding device 20 decodes the received compression signal (Sc) of the electrocardiographic signal S using the above-described expansion and decoding method. Then, the biological information decoding device 20 outputs the decoded electrocardiographic signal S to the output device 5. Note that the internal configuration and more detailed operation (function) of the biological information decoding device 20 are described later.

[Biological Information Processing Device]

(1) Example of Basic Configuration

Figure 6:
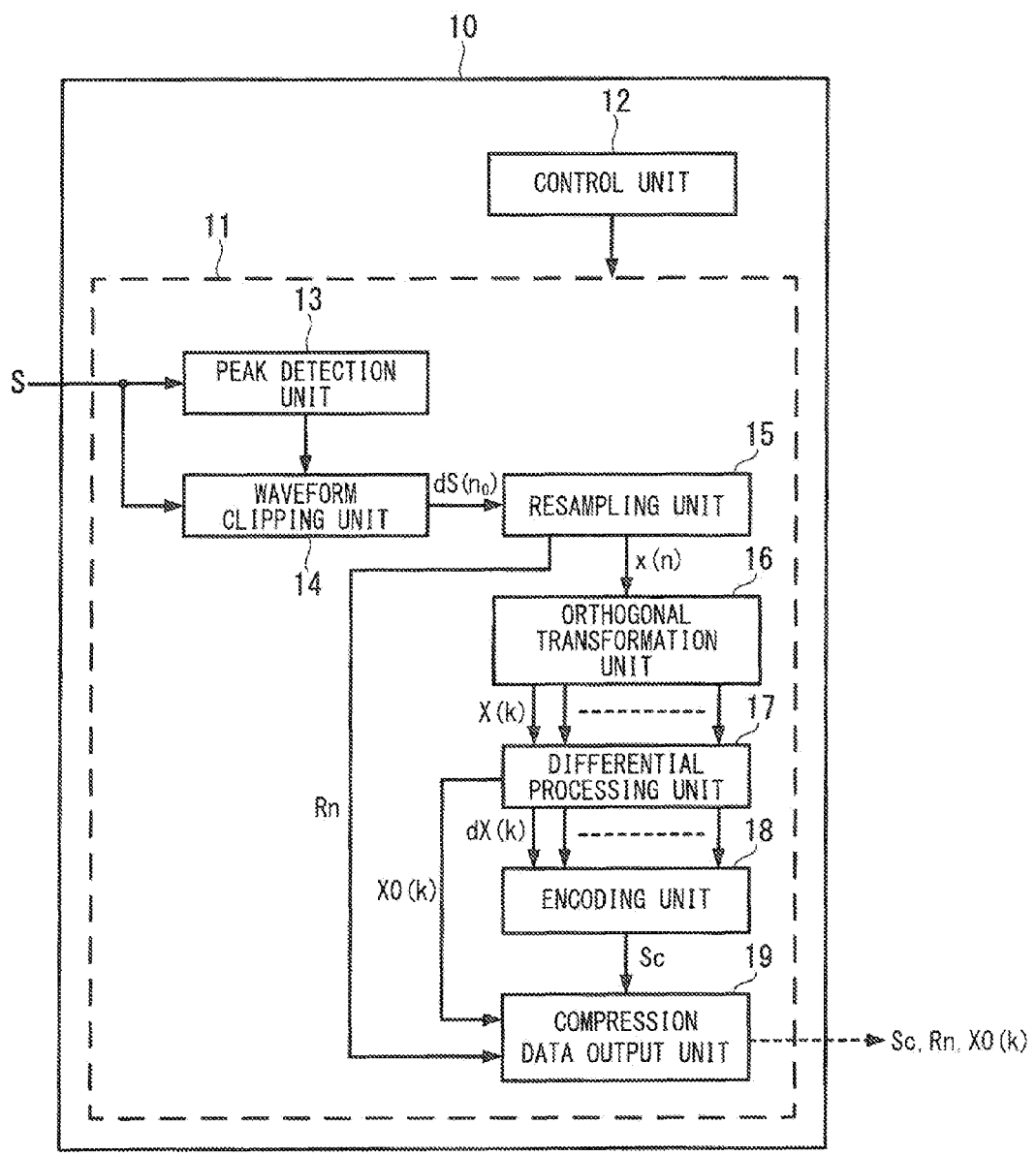
FIG. 6 is a general block configuration diagram of a biological information processing device (basic configuration example) according to an embodiment of the present invention.

Next, the basic configuration of the inside of the biological information processing device 10 and the function of each unit are described with reference to FIG. 6. FIG. 6 is the internal block configuration diagram of the biological information processing device 10. In FIG. 6, for simplicity of description, only the configuration involving in electrocardiographic information compression processing is mainly illustrated.

The biological information processing device 10 includes a compression module unit 11 and a control unit 12. Note that, the biological information processing device 10 may include a storage unit for storing data, such as the compressed electrocardiographic signal Sc, a resampling rate Rn to be described later, and an initial value X0($k$) of the orthogonal transformation coefficient X(k) to be described later.

The compression module unit 11 includes a peak detection unit 13, a waveform clipping unit 14, a resampling unit 15, an orthogonal transformation unit 16, a differential processing unit 17, an encoding unit 18, and a compression data output unit 19 (transmission unit).

The peak detection unit 13 is connected to the electrocardiographic sensor 4 (see FIG. 5), and detects the peak P (see FIG. 1) of the R wave of the electrocardiographic signal S input from the electrocardiographic sensor 4. Note that, as the method for detecting the peak P of the R wave of the electrocardiographic signal S in the peak detection unit 13, any method used in the conventional signal processing is used. The peak detection unit 13 is connected to the waveform clipping unit 14, and outputs the detection result of the peak P to the waveform clipping unit 14. For example, the peak detection unit 13 outputs a signal with the waveform, in which a pulse is generated at a timing corresponding to the peak P of the R wave, to the waveform clipping unit 14 as the detection result of the peak P.

The waveform clipping unit 14 is connected to the electrocardiographic sensor 4 and the peak detection unit 13. Based on the detection result of the peak P of the R wave of the electrocardiographic signal S input from the peak detection unit 13, the waveform clipping unit 14 clips out the inter-peak electrocardiographic signal dS(n0) (a first peak-to-peak biological signal) as illustrated in FIG. 2, for example. Moreover, the waveform clipping unit 14 is connected to the resampling unit 15, and outputs the clipped inter-peak electrocardiographic signal dS(n0) to the resampling unit 15. Specifically, based on the peak detection result input from the peak detection unit 13, the waveform clipping unit 14 outputs the actual data (dS(n0)) between the peak P of the R wave at a prescribed time and the peak P of the next R wave to the resampling unit 15.

Using a method, such as the Lagrange's method or the spline method, the resampling unit 15 transforms (resamples)

the inter-peak electrocardiographic signal dS(n0) of the number of samples NO, which is input from the waveform clipping unit 14, to the inter-peak electrocardiographic signal x(n) (a second peak-to-peak biological signal) of the prescribed number of samples N (e.g., N=512). The resampling unit 15 also calculates the resampling rate Rn (=N0/N) of the inter-peak electrocardiographic signal dS(n0).

The resampling unit 15 is connected to the orthogonal transformation unit 16 and outputs the normalized inter-peak electrocardiographic signal x(n) to the orthogonal transformation unit 16. Moreover, the resampling unit 15 is connected to the compression data output unit 19, and outputs the resampling rate Rn corresponding to the inter-peak electrocardiographic signal x(n), which is output to the orthogonal transformation unit 16, to the compression data output unit 19. Note that, in this case, the resampling unit 15 may output the number of samples NO of the corresponding inter-peak electrocardiographic signal dS(n0), in place of the resampling rate Rn, to the compression data output unit 19.

The orthogonal transformation unit 16, using a method, such as DCT and MDCT, divides the normalized inter-peak electrocardiographic signal x(n), which is input from the resampling unit 15, into a prescribed number of frequency bands, and performs orthogonal transformation on the resulting signal to generate the orthogonal transformation coefficient X(k) (k=0 to N−1). Note that, in the embodiment, the normalized inter-peak electrocardiographic signal x(n) is divided into the same number of frequency bands as the number of samples N. Moreover, the orthogonal transformation unit 16 is connected to the differential processing unit 17 and outputs the generated orthogonal transformation coefficient X(k) to the differential processing unit 17.

The differential processing unit 17 generates the differential signal dX(k) on the time axis of the orthogonal transformation coefficient X(k) that is input from the orthogonal transformation unit 16. Moreover, the differential processing unit 17 is connected to the encoding unit 18 and outputs the generated differential signal dX(k) to the encoding unit 18. Furthermore, the differential processing unit 17 is connected to the compression data output unit 19, and outputs to the compression data output unit 19 the orthogonal transformation coefficient X(k) of the peak electrocardiographic signal x(n) to be processed first on the time axis (i.e., the initial value X0($k$) of the orthogonal transformation coefficient X(k)). Note that the initial value X0($k$) of the orthogonal transformation coefficient X(k) is used in decoding the orthogonal transformation coefficient X(k) from the differential signal dX(k) in the biological information decoding device 20.

The encoding unit 18 performs prescribed encoding processing, such as entropy encoding processing, on the differential signal dX(k) of the orthogonal transformation coefficient X(k) input from the differential processing unit 17, to encode the differential signal dX(k). The encoding unit 18 is connected to the compression data output unit 19, and outputs the encoded signal, i.e., the compressed electrocardiographic signal Sc, to the compression data output unit 19.

The compression data output unit 19 applies a prescribed modulation to the compressed electrocardiographic signal Sc input from the encoding unit 18, to the resampling rate Rn input from the resampling unit 15, and to the initial value X0($k$) of the orthogonal transformation coefficient X(k) input from the differential processing unit 17, to generate a transmission signal. Then, the compression data output unit 19 transmits the generated transmission signal to the biological information decoding device 20. Note that, in this case, the compression data output unit 19 may transmit a corresponding transmission signal for each R-R period to the biological information decoding device 20, or may store the data of the compressed electrocardiographic signal Sc, which is input from the encoding unit 18, for a prescribed period and then transmit these data collectively to the biological information decoding device 20.

The control unit 12 is constituted by a calculation unit, such as a CPU (Central Processing Unit), which controls the whole operation of the biological information processing device 10. Then, in the embodiment, the control unit 12 controls the operation of each unit inside the compression module unit 11 described above, i.e., the operation of electrocardiographic information compression processing.

(2) Variant

In transmitting a transmission signal to the biological information decoding device 20 from the compression data output unit 19, when the information transmission amount of a transmission path is defined in advance, and when the information amount of a transmission signal output from the compression data output unit 19 exceeds the defined information transmission amount, quantization processing may be preferably further performed on the orthogonal transformation coefficient X(k) of the normalized inter-peak electrocardiographic signal x(n).

Figure 7:
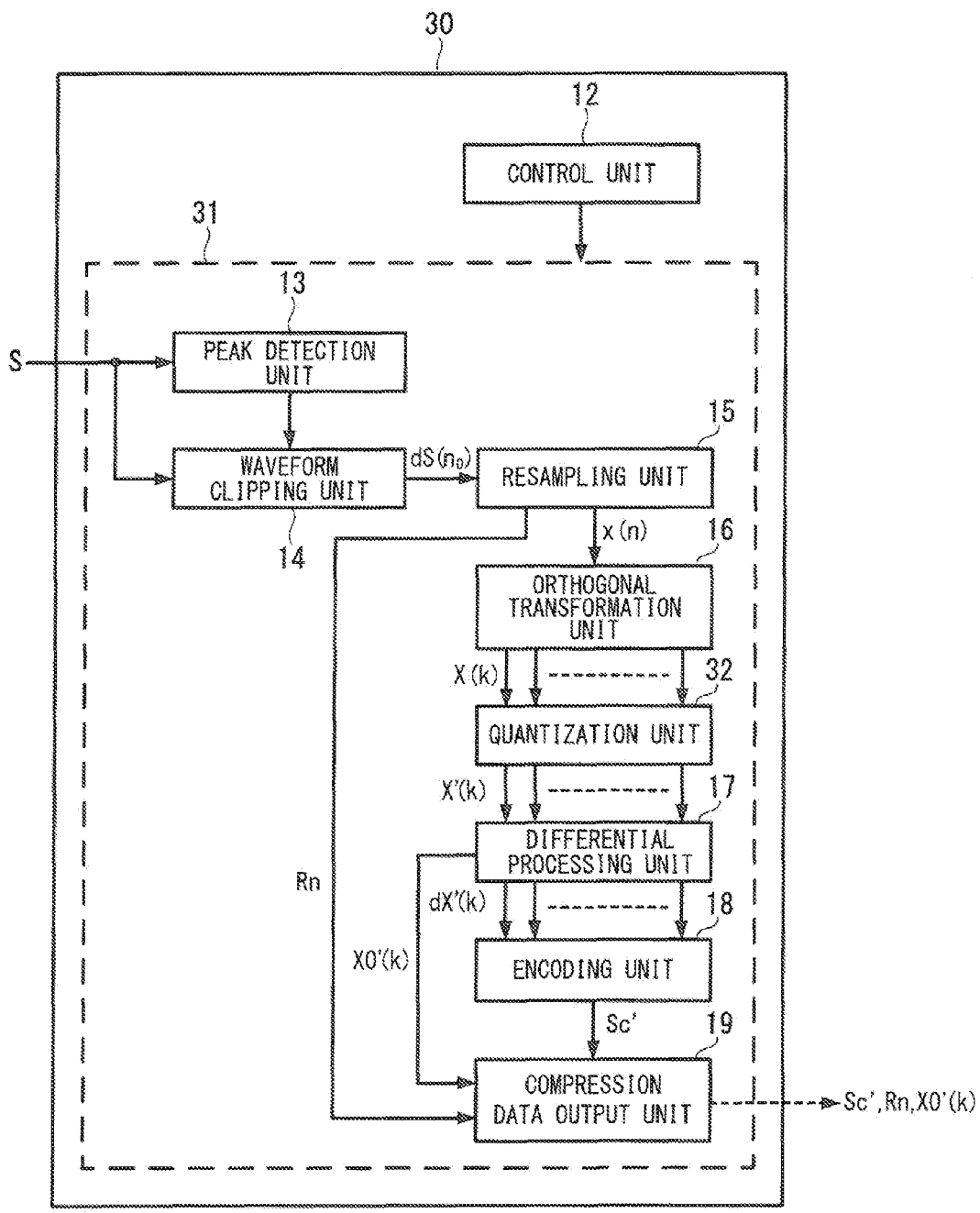
FIG. 7 is a general block configuration diagram of a biological information processing device of a variant.

FIG. 7 illustrates an example (variant) in this case. FIG. 7 is the general configuration block diagram of a biological information processing device 30 of the variant. Moreover, in the biological information processing device 30 illustrated in FIG. 7, the same reference numeral is attached to the same component as that in the biological information processing device 10 of the above-described embodiment (basic configuration example) illustrated in FIG. 6.

As apparent from the comparison between FIG. 7 and FIG. 6, the biological information processing device 30 of this example has the configuration in which a quantization unit 32 is provided between the orthogonal transformation unit 16 and the differential processing unit 17 in the biological information processing device 10 of the above-described embodiment. In this example, the configuration other than the quantization unit 32 inside a compression module unit 31 is the same as the corresponding configuration of the biological information processing device 10 of the above-described embodiment.

The quantization unit 32 quantizes (rounds off) the orthogonal transformation coefficient X(k), which is input from the orthogonal transformation unit 16, and transforms it into a discrete integer value defined by a prescribed quantization step size. That is, the quantization unit 32 further discretizes the orthogonal transformation coefficient X(k), which is input from the orthogonal transformation unit 16, to reduce the data amount thereof.

As described above, in the configuration of this example, the data amount of a transmission signal can be further reduced by the quantization unit 32. Therefore, even in a system in which the information transmission amount is defined in advance, electrocardiographic information can be easily transmitted from the compression data output unit 19 to the biological information decoding device 20.

Note that, in the example illustrated in FIG. 7, an example has been described in which the quantization processing is performed on the orthogonal transformation coefficient X(k), but the present invention is not limited thereto. The quantization processing may be performed on the differential signal dX(k) of the orthogonal transformation coefficient X(k). In this case, the quantization unit 32 is provided between the differential processing unit 17 and the encoding unit 18. Moreover, in the case where in the differential processing unit 17 the differential signal dX(k) is calculated using a method, such as ADPCM, the quantization unit 32 may not be provided because the quantization processing is performed substantially inside the differential processing unit 17.

In the above-described embodiment and variant, each unit of the compression module unit may be constituted by hardware so as to realize the above-described electrocardiographic information compression processing, but the above-described electrocardiographic information compression processing may be executed using a prescribed compression processing program (software). In this case, the compression processing program is stored into a storage unit, such as a non-illustrated ROM (Read Only Memory) inside the biological information processing device. Then, when the compression processing is executed, the control unit 12 reads (expands) the compression processing program to a non-illustrated RAM (Random Access Memory), and performs the above-described electrocardiographic information compression processing.

Moreover, in the case where the compression processing program is used, the compression processing program may be installed into a storage unit in advance, or the compression processing program may be separately installed into the biological information processing device from the outside so as to execute the above-described compression processing. In the latter case, the compression processing program may be distributed from a medium, such as an optical disk or a semiconductor memory, or may be downloaded via transmission means, such as the Internet.

[Biological Information Decoding Device]

Figure 8:
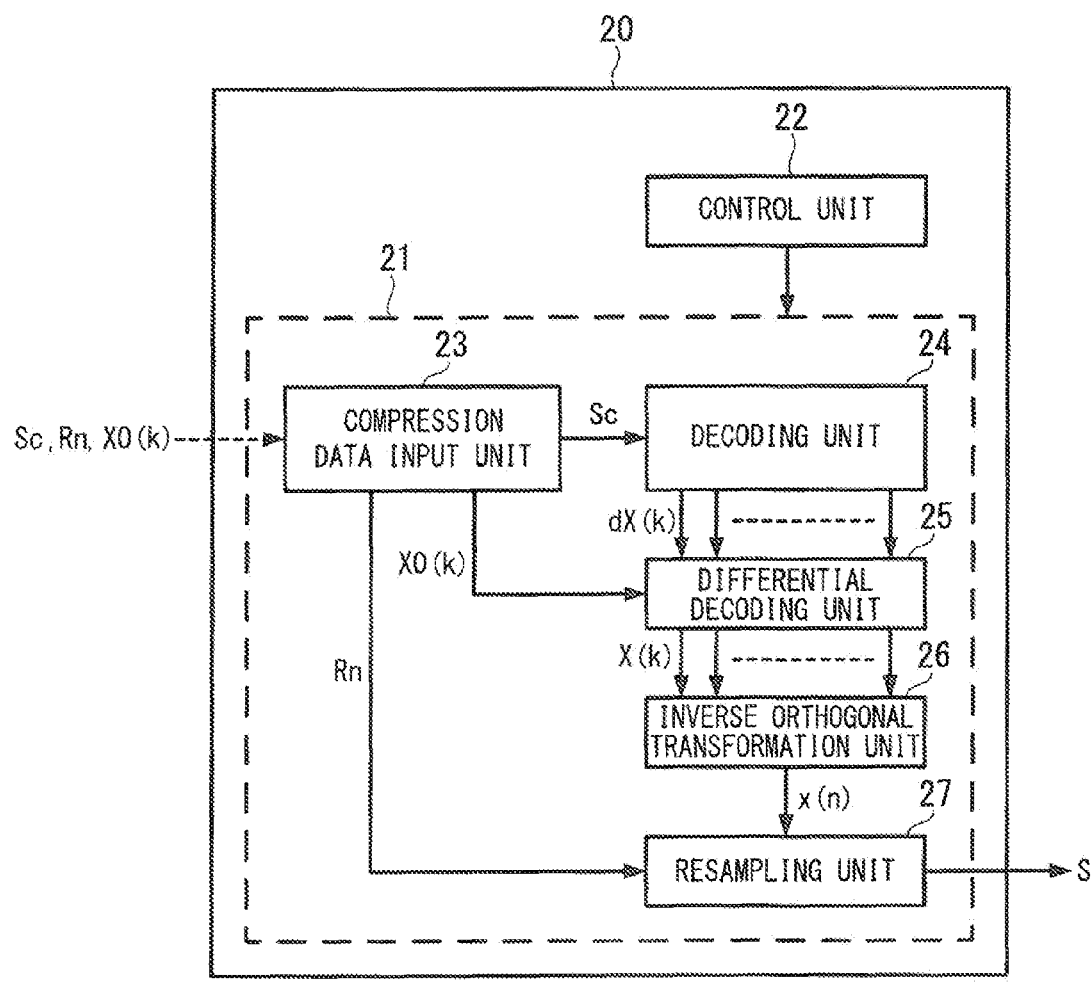
FIG. 8 is a general block configuration diagram of a biological information decoding device according to an embodiment of the present invention.

Next, the internal configuration of the biological information decoding device 20 and the function of each unit are described with reference to FIG. 8. FIG. 8 is the internal block configuration diagram of the biological information decoding device 20. In FIG. 8, for simplicity of description, only the configuration involving in the electrocardiographic information expansion and decoding processing are mainly illustrated.

The biological information decoding device 20 includes a decoding module unit 21 and a control unit 22. Note that, the biological information decoding device 20 may include a storage unit for storing data, such as the compressed electrocardiographic signal Sc, the resampling rate Rn, and the initial value $X0(k)$ of the orthogonal transformation coefficient $X(k)$, which are transmitted from the biological information processing device 10.

The decoding module unit 21 includes a compression data input unit 23 (receiving unit), a decoding unit 24, a differential decoding unit 25, an inverse orthogonal transformation unit 26, and a resampling unit 27.

The compression data input unit 23 receives data of, the compressed electrocardiographic signal Sc, the resampling rate Rn, and the initial $X0(k)$ of the orthogonal transformation coefficient $X(k)$, which are transmitted from the biological information processing device 10 (compression data output unit 19), and demodulates the received signal.

The compression data input unit 23 is connected to the decoding unit 24 and outputs the compression data (Sc) of the demodulated electrocardiographic signal S to the decoding unit 24. Moreover, the compression data input unit 23 is connected to the resampling unit 27 and outputs the data of the demodulated resampling rate Rn to the resampling unit 27. Furthermore, the compression data input unit 23 is connected to the differential decoding unit 25 and outputs the initial value $X0(k)$ of the demodulated orthogonal transformation coefficient $X(k)$ to the differential decoding unit 25.

The decoding unit 24 performs a prescribed decoding processing on the compressed electrocardiographic signal Sc that is input from the compression data input unit 23, to decode the differential signal $dX(k)$ on the time axis of the orthogonal transformation coefficient $X(k)$ ($k=0$ to $N-1$). Note that, in this case, the decoding unit 24 decodes the differential signal $dX(k)$ using a decoding method corresponding to the encoding method that is used in compressing the electrocardiographic signal S. Moreover, the decoding unit 24 is connected to the differential decoding unit 25 and outputs the decoded differential signal $dX(k)$ to the differential decoding unit 25.

The differential decoding unit 25 calculates the orthogonal transformation coefficient $X(k)$, based on the time series data of the differential signal $dX(k)$ input from the decoding unit 24 and the initial value $X0(k)$ of the orthogonal transformation coefficient $X(k)$ input from the compression data input unit 23. Note that, in this case, the differential decoding unit 25 decodes the orthogonal transformation coefficient $X(k)$ using a decoding method corresponding to the method for calculating the differential signal $dX(k)$ that is used in compressing the electrocardiographic signal S. Moreover, the differential decoding unit 25 is connected to the inverse orthogonal transformation unit 26 and outputs the calculated orthogonal transformation coefficient $X(k)$ to the inverse orthogonal transformation unit 26.

The inverse orthogonal transformation unit 26 performs a prescribed inverse orthogonal transformation processing on the orthogonal transformation coefficient $X(k)$ input from the differential decoding unit 25, to transform the orthogonal transformation coefficient $X(k)$ (signal in the frequency domain) to the normalized inter-peak electrocardiographic signal $x(n)$ (signal in the time domain). Note that, in this case, the inverse orthogonal transformation unit 26 calculates the inter-peak electrocardiographic signal $x(n)$ using an inverse orthogonal transformation method corresponding to the orthogonal transformation method that is used in compressing the electrocardiographic signal S. Moreover, the inverse orthogonal transformation unit 26 is connected to the resampling unit 27 and outputs the normalized inter-peak electrocardiographic signal $x(n)$ to the resampling unit 27.

Based on the normalized inter-peak electrocardiographic signal $x(n)$ input from the inverse orthogonal transformation unit 26 and the resampling rate Rn ($=N0/N$) in the R-R period corresponding to this inter-peak electrocardiographic signal $x(n)$ input from the compression data input unit 23, the resampling unit 27 resamples this inter-peak electrocardiographic signal $x(n)$ with the number of samples NO to decode the corresponding inter-peak electrocardiographic signal $dS(n0)$ (actual data). Moreover, the resampling unit 27 is connected to the output device 5 and sequentially outputs the decoded inter-peak electrocardiographic signal $dS(n0)$ to the output device 5. Thus, the decoded electrocardiographic signal S is output to the output device 5 from the biological information decoding device 20.

Note that, in the above-described embodiment, each unit inside the decoding module unit 21 may be constituted by hardware so as to realize the above-described electrocardiographic information decoding processing, or the above-described electrocardiographic information decoding processing may be executed using a prescribed decoding processing program (software). In this case, the decoding processing program is stored into a storage unit, such as a non-illustrated ROM inside the biological information decoding device 20. Then, when the decoding processing is executed, the control unit 22 reads (expands) the decoding processing program to a non-illustrated RAM, and performs the above-described electrocardiographic information decoding processing.

Moreover, in the case where the decoding processing program is used, the decoding processing program may be installed into the storage unit in advance, or the decoding processing program may be separately installed into the biological information decoding device 20 from the outside so as to execute the above-described decoding processing. In the latter case, the decoding processing program may be distributed from a medium, such as an optical disk or a semiconductor memory, or may be downloaded via transmission means, such as the Internet.

<3. Example of Operation of Biological Information Processing System>

[Compression Operation]

Figure 9:
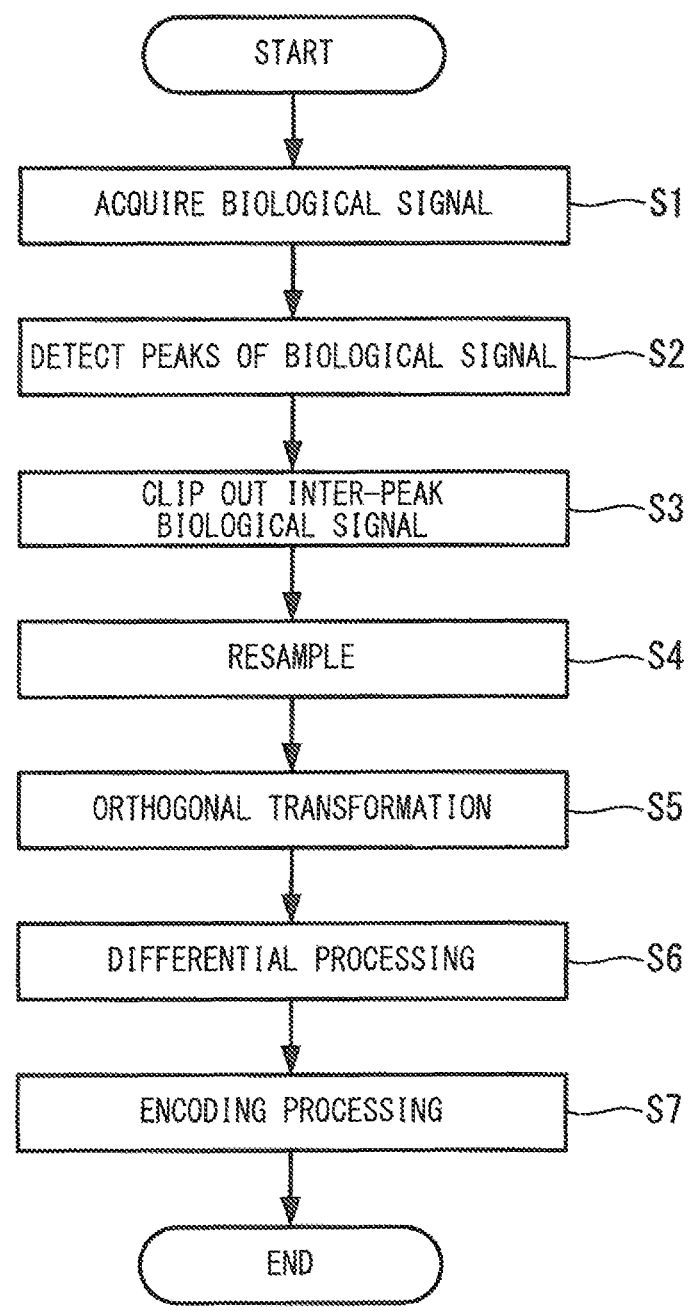
FIG. 9 is a flow chart illustrating a procedure of electrocardiographic information compression processing in the biological information processing device according to an embodiment of the present invention.

Next, the electrocardiographic information compression processing operation in the biological information processing system 1 (biological information processing device 10) of the embodiment is briefly described with reference to FIG. 9. FIG. 9 is the flow chart illustrating the procedure of the electrocardiographic information compression processing operation performed by the biological information processing device 10.

Note that, in the embodiment, in the case where the compression module unit 11 inside the biological information processing device 10 is constituted by hardware, the control unit 12 controls each unit inside the compression module unit 11 to execute an electrocardiographic information compression operation described below. Moreover, when the electrocardiographic information compression operation described below is executed using a compression processing program, the control unit 12 reads the compression processing program to a RAM (not illustrated) and executes the compression operation.

In the electrocardiographic information compression operation, first, as illustrated in FIG. 9, the biological information processing device 10 acquires the electrocardiographic signal S from the electrocardiographic sensor 4 (Step S1). Next, the biological information processing device 10 detects the peak P of the R wave of the acquired electrocardiographic signal S (Step S2). Next, the biological information processing device 10 clips out the inter-peak electrocardiographic signal dS(n0) from the electrocardiographic signal S based on the detection result of the peak P of the R wave of the electrocardiographic signal S in Step S2 (Step S3).

Next, the biological information processing device 10 resamples the clipped inter-peak electrocardiographic signal dS(n0) with the prescribed number of samples N using a method, such as the Lagrange's method or the spline method (Step S4). With this resampling processing, the normalized inter-peak electrocardiographic signal x(n) is generated and a fluctuation in the peak position of the R wave generated in actual data of the electrocardiographic signal S (a fluctuation of the R-R period) can be removed.

Next, the biological information processing device 10, using a method, such as DCT or MDCT, divides the normalized inter-peak electrocardiographic signal x(n) into the same number of frequency bands as the number of samples N to perform orthogonal transformation (Step S5). In the embodiment, in the normalized inter-peak electrocardiographic signal x(n), a fluctuation in the peak position of the R wave generated in actual data of the electrocardiographic signal S (a fluctuation of the R-R period) is removed. Therefore, the value of the orthogonal transformation coefficient X(k) generated in Step S5 varies continuously and gently with respect to time as described in FIG. 4.

Next, the biological information processing device 10 generates the differential signal dX(k) on the time axis of the orthogonal transformation coefficient X(k) (Step S6). This differential processing generates the time series data of the differential signal dX(k) having a data format that can be easily compressed at a higher compression rate. Next, the biological information processing device 10 encodes the differential signal dX(k) using a conventionally known encoding method, such as the entropy encoding method (Step S7).

In the embodiment, the electrocardiographic information (electrocardiographic signal S) is compressed in this manner. Then, the biological information processing device 10 transmits the compression data (Sc) of the electrocardiographic signal S generated as described above, the resampling rate Rn of the inter-peak electrocardiographic signal dS(n0) for each R-R period, and the initial value $X0(k)$ of the orthogonal transformation coefficient X(k) to the biological information decoding device 20.

Note that, in the biological information processing device 30 (variant) including the quantization unit 32 as illustrated in FIG. 7, quantization processing is performed between the above-described Step S5 and Step S6 or between the above-described Step S6 and Step S7. Specifically, the biological information processing device 30 performs quantization processing on the orthogonal transformation coefficient X(k) generated in Step S5 or on the differential signal dX(k) generated in Step S6.

[Expansion and Decoding Operation]

Next, the electrocardiographic information expansion and decoding processing operation in the biological information processing system 1 (biological information decoding device 20) of the embodiment is briefly described with reference to FIG. 10. FIG. 10 is a flow chart illustrating the procedure of the electrocardiographic information expansion and decoding processing operation performed by the biological information decoding device 20.

Note that, in the embodiment, in the case where the decoding module unit 21 inside the biological information decoding device 20 is constituted by hardware, the control unit 22 controls each unit inside the decoding module unit 21 to execute the electrocardiographic information expansion and decoding operation described below. Moreover, when the electrocardiographic information expansion and decoding operation described below is executed using a decoding processing program, the control unit 22 reads the decoding processing program to a RAM (not shown) and executes the expansion and decoding operation.

In the electrocardiographic information expansion and decoding operation, first, as illustrated in FIG. 10, the biological information decoding device 20 receives a transmission signal transmitted from the biological information processing device 10, and demodulates the received signal. Thus, the biological information decoding device 20 acquires the compression data (Sc) of the electrocardiographic signal S, the resampling rate Rn of the inter-peak electrocardiographic signal dS(n0) for each R-R period, and the initial value $X0(k)$ of the orthogonal transformation coefficient X(k) (Step S11).

Next, the biological information decoding device 20 performs a prescribed decoding processing on the compression data (Sc) of the electrocardiographic signal S to generate the differential signal dX(k) of the orthogonal transformation coefficient X(k) (Step S12). Note that, in this case, the compression data (Sc) of the electrocardiographic signal S is decoded using a decoding method corresponding to the encoding method that is used in compressing the electrocardiographic signal S. For example, in the case where an entropy encoding method is used in compressing the electrocardiographic signal S, the biological information decoding device 20 decodes the compression data using the entropy decoding method.

Next, the biological information decoding device 20 performs a prescribed differential decoding processing based on the time series data of the differential signal dX(k) generated in Step S12 and the initial value X0(k) of the orthogonal transformation coefficient X(k) acquired in Step S11 to calculate the orthogonal transformation coefficient X(k) (Step S13). Note that, in this case, the biological information decoding device 20 calculates the orthogonal transformation coefficient X(k) using a differential decoding method corresponding to the differential method that is used in compressing the electrocardiographic signal S. For example, in the case where the differential signal dX(k) is generated by ADPCM in compressing the electrocardiographic signal S, the biological information decoding device 20 decodes the orthogonal transformation coefficient X(k) by ADPCM.

Next, the biological information decoding device 20 performs a prescribed inverse orthogonal transformation processing on the orthogonal transformation coefficient X(k), to transform the orthogonal transformation coefficient X(k) (signal in the frequency domain) to the normalized inter-peak electrocardiographic signal x(n) (signal in the time domain) (Step S14). Note that, in this case, the biological information decoding device 20 calculates the normalized inter-peak electrocardiographic signal x(n) using an inverse orthogonal transformation method corresponding to the orthogonal transformation method that is used in compressing the electrocardiographic signal S. For example, in the case where the orthogonal transformation coefficient X(k) is generated by MDCT in compressing the electrocardiographic signal S, the biological information decoding device 20 transforms the orthogonal transformation coefficient X(k) to the inter-peak electrocardiographic signal x(n) by IMDCT.

Then, the biological information decoding device 20 resamples the normalized inter-peak electrocardiographic signal x(n) with the number of samples NO of actual data, based on the resampling rate Rn of the inter-peak electrocardiographic signal dS(n0) acquired in Step S11 (Step S15). Thus, the inter-peak electrocardiographic signal dS(n0) (actual data) is decoded.

Subsequently, the inter-peak electrocardiographic signals dS(n0) are combined in chronological order to decode the electrocardiographic signal S. In the embodiment, the electrocardiographic information (electrocardiographic signal S) is decoded in this manner.

As described above, in the embodiment, the actual data (dS(n0)) of the inter-peak electrocardiographic signal is normalized so as to remove a fluctuation in the peak position of the R wave generated in actual data of the electrocardiographic signal S (a fluctuation of the R-R period). Then, furthermore, the encoding processing is performed on the differential signal (d) of the orthogonal transformation coefficient X(k) of the normalized inter-peak electrocardiographic signal x(n) to compress the electrocardiographic signal S. Therefore, in the biological information processing device 10 and biological information processing system 1 of the embodiment, the biological information can be compressed at a higher compression rate.

Note that, in the above-described embodiment, a system has been taken as an example and described, in which the compression data (Sc) of the electrocardiographic signal S is transmitted via communication between the biological information processing device 10 and the biological information decoding device 20, but the present invention is not limited thereto.

For example, the present invention can be applied also to a biological information processing system, in which the biological information processing device 10 and the biological information decoding device 20 are integrally provided and in which without modulating the compression data (Sc) of the electrocardiographic signal S, the compression data (Sc) is directly transmitted to the biological information decoding device 20 from the biological information processing device 10. Here, the same effect can be obtained. In this case, the compression data output unit 19 of the biological information processing device 10 and the compression data input unit 23 of the biological information decoding device 20 may be constituted by, for example, an I/O (Input/Output) interface and the both may be electrically and directly connected to each other.

Moreover, for example, a storage unit, in place of the compression data output unit 19, may be provided in the biological information processing device 10 whereby the data, such as the compressed electrocardiographic signal Sc, the resampling rate Rn of the inter-peak electrocardiographic signal dS(n0), and the initial value X0(k) of the orthogonal transformation coefficient X(k), may be stored into this storage unit without being transmitted outside.

REFERENCE SIGNS LIST

1 . . . biological information processing system, 2 . . . transmission-side device, 3 . . . receiving-side device, 4 . . . electrocardiographic sensor, 5 . . . output device, 10 . . . biological information processing device, 11 . . . compression module unit, 12 . . . control unit, 13 . . . peak detection unit, 14 . . . waveform clipping unit, 15 . . . resampling unit, 16 . . . orthogonal transformation unit, 17 . . . differential processing unit, 18 . . . encoding unit, 19 . . . compression data output unit, 20 . . . biological information decoding device, 21 . . . decoding module unit, 22 . . . control unit, 23 . . . compression data input unit, 24 . . . decoding unit, 25 . . . differential decoding unit, 26 . . . inverse orthogonal transformation unit, 27 . . . resampling unit

The invention claimed is:
1. A biological information processing device, comprising:
a peak detection unit configured to detect peaks of a biological signal generated in a cardiac cycle;
a waveform clipping unit configured to clip out a first peak-to-peak biological signal between two peaks, which are adjacent on a time axis of the biological signal, on the basis of detection results of the peak detection unit;
a resampling unit configured to transform the first peak-to-peak biological signal to a second peak-to-peak biological signal of a prescribed number of samples;
an orthogonal transformation unit configured to generate orthogonal transformation coefficients by performing an orthogonal transformation on the second peak-to-peak biological signal;
a differential processing unit configured to generate a differential signal of the orthogonal transformation coefficients on the time axis; and
an encoding unit configured to encode the differential signal.

2. The biological information processing device according to claim 1, further comprising a transmission unit configured to transmit a signal encoded by the encoding unit to an external device.

3. The biological information processing device according to claim 1, further comprising a quantization unit configured to quantize the orthogonal transformation coefficient or the differential signal.

4. The biological information processing device according to claim 1, wherein the peak of the biological signal is a peak of an R wave of an electrocardiographic signal.

5. The biological information processing device according to claim 1, wherein the number of samples of the first peak-to-peak biological signal to be clipped out by the waveform clipping unit varies depending on a time zone to be clipped out.

6. The biological information processing device according to claim 1, wherein the resampling unit transforms the first peak-to-peak biological signal to the second peak-to-peak biological signal of the prescribed number of samples using a Lagrange's method or a spline method.

7. The biological information processing device according to claim 1, wherein the resampling unit calculates a resampling rate of the first peak-to-peak biological signal.

8. The biological information processing device according to claim 1, wherein the orthogonal transformation unit divides the second peak-to-peak biological signal into a prescribed number of frequency bands to perform orthogonal transformation using any method of DCT, MDCT, LOT and WHT, thereby generating the orthogonal transformation coefficients.

9. The biological information processing device according to claim 1, wherein the differential processing unit generates a difference value, as the differential signal, between the orthogonal transformation coefficient at a prescribed time and the orthogonal transformation coefficient at a time one sample earlier than the prescribed time or at a time one sample later than the prescribed time on the time axis.

10. The biological information processing device according to claim 1, wherein the differential processing unit calculates a difference value between the orthogonal transformation coefficient at a prescribed time and the orthogonal transformation coefficient at a time one sample earlier than the prescribed time or at a time one sample later than the prescribed time on the time axis, and encodes the difference value using a method of DPCM or ADPCM to generate the encoded signal as the differential signal.

11. A biological information processing system, comprising:
   a biological information processing device including:
      a peak detection unit configured to detect peaks of a biological signal generated in a cardiac cycle;
      a waveform clipping unit configured to clip out a first peak-to-peak biological signal between two peaks, which are adjacent on a time axis of the biological signal, on the basis of detection results of the peak detection unit;
      a resampling unit configured to transform the first peak-to-peak biological signal to a second peak-to-peak biological signal of a prescribed number of samples;
      an orthogonal transformation unit configured to generate orthogonal transformation coefficients by performing an orthogonal transformation on the second peak-to-peak biological signal;
      a differential processing unit configured to generate a differential signal of the orthogonal transformation coefficients on the time axis; and
      an encoding unit configured to encode the differential signal; and
   a biological information decoding device configured to decode the biological signal from a signal encoded by the encoding unit.

12. The biological information processing system according to claim 11, wherein
   the biological information processing device includes a transmission unit configured to transmit the signal encoded by the encoding unit, to the biological information decoding device, and wherein
   the biological information decoding device includes a receiving unit configured to receive the encoded signal that is transmitted from the biological information processing device.

* * * * *